United States Patent [19]

Homsma et al.

[11] Patent Number: 5,976,172
[45] Date of Patent: Nov. 2, 1999

[54] RETRACTABLE TEMPORARY VENA CAVA FILTER

[75] Inventors: Tjeerd Homsma, Roden; Alexander Christiaan Boudewijn, Leek, both of Netherlands

[73] Assignee: Cordis Corporation, Miami Lakes, Fla.

[21] Appl. No.: 08/887,191

[22] Filed: Jul. 2, 1997

[30] Foreign Application Priority Data

Jul. 3, 1996 [NL] Netherlands ............................ 1003497

[51] Int. Cl.$^6$ .................................................. A61M 29/00
[52] U.S. Cl. .......................... 606/200; 604/104; 606/191
[58] Field of Search ..................................... 600/200, 127, 600/169, 191, 198; 604/104, 105, 106

[56] References Cited

U.S. PATENT DOCUMENTS

| | | |
|---|---|---|
| 3,952,747 | 4/1976 | Kimmell, Jr. . |
| 4,425,908 | 1/1984 | Simon . |
| 4,494,531 | 1/1985 | Gianturco . |
| 4,723,549 | 2/1988 | Wholey et al. . |
| 4,793,348 | 12/1988 | Palmaz . |
| 4,832,055 | 5/1989 | Palestrant . |
| 4,957,501 | 9/1990 | Lahille et al. . |
| 4,990,156 | 2/1991 | Lefebvre . |
| 5,133,733 | 7/1992 | Rasmussen et al. . |
| 5,324,304 | 6/1994 | Rasmussen . |
| 5,329,942 | 7/1994 | Gunther et al. . |
| 5,421,832 | 6/1995 | Lefebvre .................................. 606/200 |
| 5,484,424 | 1/1996 | Cottenceau et al. ..................... 606/200 |
| 5,795,322 | 8/1998 | Boudewijn ............................... 606/200 |
| 5,810,874 | 9/1998 | Lefbvre ................................... 606/200 |

FOREIGN PATENT DOCUMENTS

| | | |
|---|---|---|
| 0 437 121 | 11/1990 | European Pat. Off. . |
| 2 606 642 | 11/1986 | France . |
| 2 643 250 | 2/1989 | France . |
| 2 652 267 | 9/1989 | France . |
| 2 694 687 | 8/1992 | France . |
| 2 696 092 | 9/1992 | France . |

*Primary Examiner*—Gary Jackson
*Attorney, Agent, or Firm*—Michael W. Montgomery

[57] ABSTRACT

An intravascular catheter filter system which includes more particularly, the intravascular catheter filter system includes an outer cylindrical tubing having an inner lumen, an intermediate cylindrical tubing slidably received by the outer cylindrical tubing and an inner cylindrical member slidably received by the intermediate cylindrical tubing. The system also includes an expandable filter element comprised of a plurality of arcuate, elongate, flexible strips having proximal ends attached to the distal end of the outer cylindrical tubing and being positioned adjacent to each other so as to be of a generally cylindrical configuration. The flexible strips are normally biased outwardly from the center of the cylindrical configuration such that the strips form a generally bulbus configuration. A cylindrical filter retaining member is disposed on the distal end of the intermediate cylindrical tubing. The retaining member includes a cylindrical slot for receiving the distal tips of the flexible strips of the filter element. A locking member is disposed on the distal end of the inner cylindrical member for normally locking the distal tips of the flexible strips into the cylindrical slot of the retaining member, and upon movement of the inner cylindrical member relative to the intermediate cylindrical tubing, unlocking the distal tip of the flexible strips from the cylindrical slot in the retaining member to thereby assist in the removal of the catheter filter from a vessel.

5 Claims, 2 Drawing Sheets

RETRACTABLE TEMPORARY VENA CAVA FILTER

FIELD OF THE INVENTION

The present invention relates to an endovascular catheter having a filter element mounted thereon which may be temporarily placed in a vessel of the human body to entrap debris, such as blood thrombi, and then may be removed from the blood vessel without injury to the vessel.

SUMMARY OF THE INVENTION

Endovascular catheters are inserted into the vascular system of a patient for a wide variety of therapeutical purposes. One reason for inserting such a catheter into a vessel is to trap or immobilize particulate matter which may be floating within the fluid of the bloodstream. For example, in medical operations there is a danger of blood thrombi spreading throughout the vascular system of a patient. In this case, it may be desirable to place a filter in the bloodstream in order to catch or trap these thrombi. Filters for this purpose have heretofore been inserted into and withdrawn from the vascular system by use of a catheter which is inserted into a blood vessel.

One problem associated with previous filter systems is that there has been some difficulty in expanding and retracting the filter element once the element is placed into a desired position. In addition, there have been difficulties in maintaining the filter in an expanded position once the filter is placed into the blood vessel. Once employed many of these prior filter systems tend to retract in use thereby making the filter somewhat ineffective.

Another problem associated with such previous filter systems is that during the removal of temporary filter systems there is generally some injury to the vessel at the location where the filter is temporarily placed since tunica intima tend to grow around the filter elements during the period of time that the filter is placed in the vessel.

Previously proposed intravascular catheters including a filter are disclosed in the following U.S. patents:

| U. S. Pat. No. | Patentee |
| --- | --- |
| 5,484,424 | Cottenceau, et al. |
| 5,421,832 | Lefebvre |
| 5,329,942 | Gunther, et al. |
| 5,324,304 | Rasmussen |
| 5,133,733 | Rasmussen, et al. |
| 4,990,156 | Lefebvre |
| 4,957,501 | Lahille, et al. |
| 4,832,055 | Palestrant |
| 4,793,348 | Palmaz |
| 4,723,549 | Wholey, et al. |
| 4,494,531 | Gianturco |
| 4,425,908 | Simon |
| European Patent Publication | |
| 0437 121 A3 | Lefebvre |
| French Patent Publication No. | |
| 2 694 687 | Chevillon, et al. |
| 2 643 250 | Metais, et al. |
| 2 606 642 | Camus |

The Cottenceau et al. U.S. Pat. No. 5,484,424 discloses a blood filtering device having a catheter with longitudinally variable rigidity.

The Lefebvre U.S. Pat. No. 5,421,832 and EP 0 437 121 A3 discloses a filter catheter including an outer tube having at its distal end longitudinal notches distributed symmetrically over its periphery and defining flexible bands. An inner tube is received in the outer tube. The flexible bands are connected at their proximal ends to the distal of the outer tube and at their distal ends to the distal end of the inner tube and open out transversely to an opened out form and/or a helical form.

The Gunther, et al. U.S. Pat. No. 5,329,942 discloses a positioning assembly having a filter distally attached thereto which is guided through a catheter to position the filter at a location beyond the distal end of the catheter and within a blood vessel.

The Rasmussen U.S. Pat. No. 5,234,304 discloses an introduction catheter for a collapsible, self-expandable implant of the type comprising a number of spring biased anchoring legs, e.g., a filter for entrapping thrombi or emboli in a blood vessel.

The Rasmussen, et al. U.S. Pat. No. 5,133,733 discloses a cooapsible filter for introduction into the blood vessel of a patient. The filter comprises a number of legs diverging from an apical hub and each having a reversely turned hook at its distal end.

The Lefebvre U.S. Pat. No. 4,990,156 discloses a filter and catheter for positioning and using the filter. The filter has a filtering section which opens out into a blood vessel when it is positioned in the blood vessel and which has no hooks for engaging the wall of the blood vessel.

The Lahille et al. U.S. Pat. No. 4,957,501 discloses an anti-embolic filter comprising a flexible wire formed into first and second substantially flat superimposed loops.

The Palestrant U.S. Pat. No. 4,832,055 discloses a blood clot filter comprising a number of peripheral wires portions of which extend between first and second connectors and free ends of which form filtering waves which anchor the filter.

The Palmaz U.S. Pat. No. 4,793,348 discloses a balloon expandable filter comprising of a tubular body the wall surface of which is partitioned by a pattern of slots into a lattice work to render the tubular body radially expandable.

The Wholey, et al. U.S. Pat. No. 4,723,549 discloses a dilatation catheter including a collapsible filter device adjacent a balloon at the distal end of the catheter and comprising a plurality of resilient ribs.

The Gianturco U.S. Pat. No. 4,494,531 discloses an expandable blood clot filter comprising a number of strands of shape memory wire which are interconnected to form a curly wire mesh.

The Simon U.S. Pat. No. 4,425,908 discloses a blood clot filter comprising a plurality of wires in the form of overlapping loops.

The Chevillon, et al. French Patent Publication NO. 2 694 687 discloses a filter assembly extendable from a catheter in which the filter assembly comprises a number of loop-shaped wire elements.

The Metais, et al. French Patent Publication No. 2 643 250 shows filter legs that are secured to the outer of an inner tube such as by means of a hub having a circular opening therein communicating with the interior lumen of the inner tube and permitting a guidewire to extend outwardly of the inner tube. The inner tube is received in an outer tube or catheter.

The Camus French Patent Publication No. 2 606 642 discloses a filament element for insertion into a vein. The filter element is defined by a distal end portion of a catheter having circumferentially spaced longitudinal slits, a hub is mounted to the distal end of the filter element and an inner rod or wire is connected to the hub for pulling the hub proximally to expand the legs formed between the slits to establish the filter in a vein.

SUMMARY OF THE PRESENT INVENTION

The catheter system of the present invention includes a catheter which is provided on its distal end with a filter element. The filter element is formed by a number of flexible strips which are distributed around the periphery and extend in longitudinal directions from the body of the catheter. The filter comprises a plurality of longitudinal strips which are biased outwardly. However, the longitudinal strips can be pressed together elastically. The catheter is carried with the filter element in the retracted position to a desired location within the bloodstream of the patient. Once the filter element is placed into the desired position, the distal end of the filter element is moved distally and the strips are bowed outwardly so as to come into contact with the walls of the vessel. Any fluid flowing through the vessel, such as blood, can flow through and between the strips but thrombi are trapped in the assembly of filter strips.

The longitudinal strips of the filter element are shaped in a generally arcuate configuration such that, when the strips are biased outwardly to contact the vessel wall, there are no sharp edges in contact with the vessel wall and therefore there is no trauma caused to the vessel wall when the filter is deployed.

More particularly, the intravascular catheter filter system includes an outer cylindrical tubing having an inner lumen, an intermediate cylindrical tubing slidably received by the outer cylindrical tubing and an inner cylindrical member slidably received by the intermediate cylindrical tubing. The system also includes an expandable filter element comprised of a plurality of arcuate, elongate, flexible strips having proximal ends attached to the distal end of the outer cylindrical tubing and being positioned adjacent to each other so as to be of a generally cylindrical configuration. The flexible strips are normally biased outwardly from the center of the cylindrical configuration such that the strips form a generally bulbus configuration. A cylindrical filter retaining member is disposed on the distal end of the intermediate cylindrical tubing. The retaining member includes a cylindrical slot for receiving the distal tips of the flexible strips of the filter element. A locking member is disposed on the distal end of the inner cylindrical member for normally locking the distal tips of the flexible strips into the cylindrical slot of the retaining member, and upon movement of the inner cylindrical member relative to the intermediate cylindrical tubing, unlocking the distal tip of the flexible strips from the cylindrical slot in the retaining member to thereby assist in the removal of the catheter filter from a vessel.

Preferably, the locking member includes a distal tip which is also received by the cylindrical slot in the retaining members to thereby releasably lock the distal tip of the flexible strips into the cylindrical slot of the retaining member.

Also, preferably the tips of the flexible strips each have an indention in the wall surface of the flexible strip, and the wall surface of the cylindrical slot in the retaining member is provided with corresponding projections which engage the indentions in the wall surface of the flexible strips. The locking member slidably engage the opposite wall surface of the distal ends of the flexible strips and the opposite wall surface of the cylindrical slot to thereby maintain the engagement between the corresponding projections in the cylindrical slot and the indentions in the distal end of corresponding flexible strips.

BRIEF DESCRIPTION OF THE DRAWINGS

The invention will be further elucidated in the following description with reference to the annexed figures herein in which.

DESCRIPTION OF A PREFERRED EMBODIMENT

Figure 1:
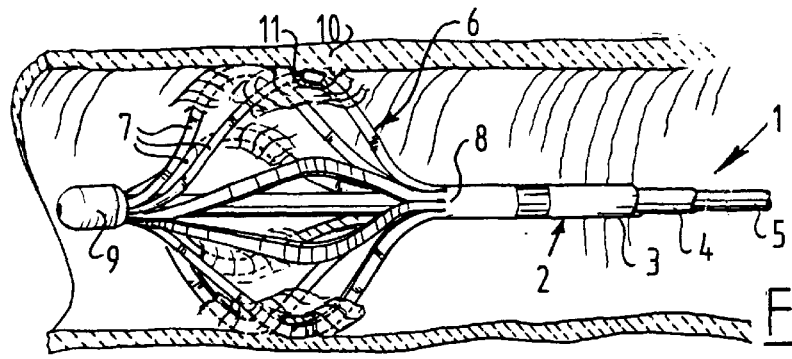
FIG. 1 illustrates a section of a catheter according to the invention for carrying the filter element after having been positioned for some time inside a vessel illustrated here in a cut-away view.

In FIG. 1 only the distal end section with the filter element 6 of the catheter 1 has been illustrated. The catheter 1 comprises a tube-like basic body 2 which comprises, in the case of this preferred embodiment, an outer tube-like element 3, a central tube-like element 4 and an inner tube-like element 5. The tube-like elements 4 and 5 are slidably positioned inside the lumens of the outer tube-like element 3 and 4, the central tube-like element respectively. As will be described in greater detail, the tube-like elements are movable in relation to one another in a longitudinal direction.

The filter element 6 comprises a plurality of pliable strips 7 arranged at equal distances from each other around the circumference of the basic body 2. The strips 7 have opposite ends which are connected to the front supporting member 9 and the rear supporting member 8, respectively. In the embodiment shown, the strips 7 have been formed by wall sections of the outer tube-like element 3, so that in this case the supporting member 8 can be considered to form an integrated part of the outer tube-like element 3 of the basic body 2.

Figure 2:
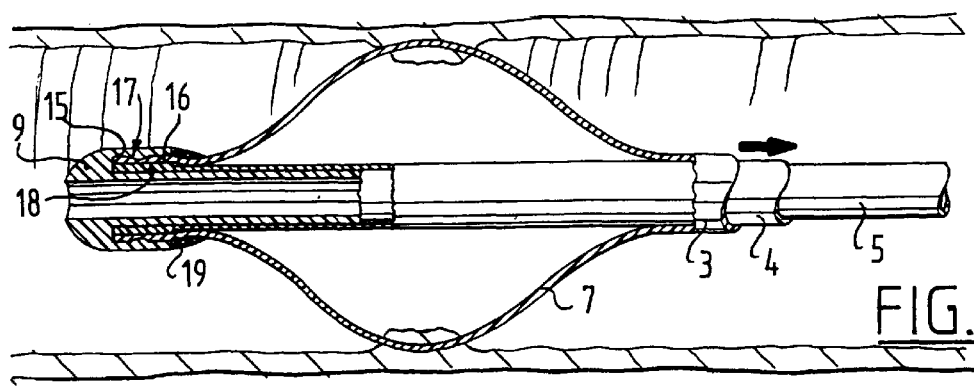
FIG. 2 illustrates the catheter of FIG. 1 in a partial longitudinal cross-section.
Figure 3:
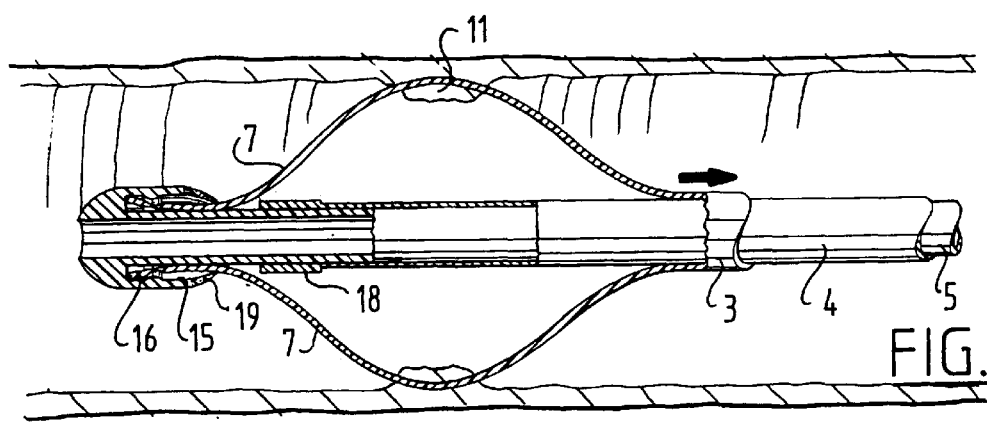
FIG. 3 illustrates a view corresponding to FIG. 2 while disengaging the strip ends.
Figure 4:
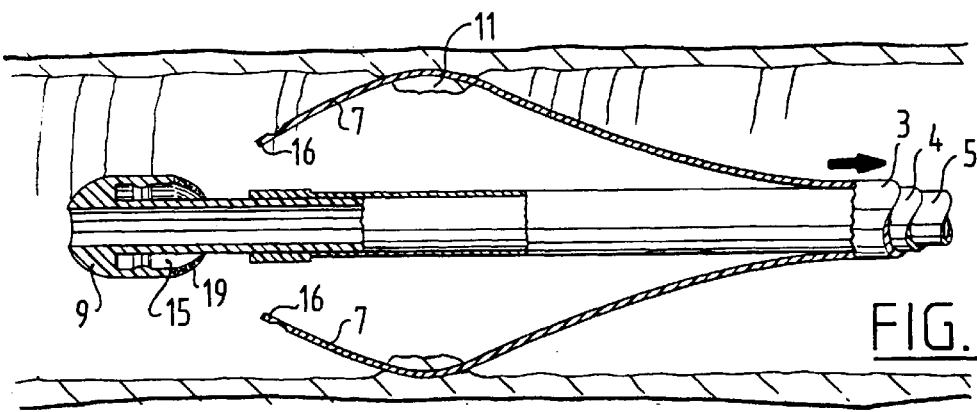
FIG. 4 illustrates a view corresponding to the FIGS. 2 and 3 after disengaging the strip ends; and, FIGS. 5 through 11 illustrates cross-sections of variations of embodiments of the catheter at the location of the supporting member to which the strips have been connected in a detachable manner.

As may be seen in FIGS. 2 through 4, the front supporting member 9 is connected to the inner tube-like element 5. Consequently the supporting members 8 and 9 may be moved both towards each other and away form each other by moving the tube-like elements 3 and 5 in the longitudinal direction in relation to each other. When the supporting members 8 and 9 are moved away from each other the strips 7 will be straightened, and when the supporting members 8 and 9 are moved towards each other the strips 7 will bend outwards as shown in FIGS. 1 through 4.

It will be clear that the catheter 1 will be introduced into a patient in the state wherein the supporting members 8 and 9 are kept at a distance from each other in order to straighten the strips, so that a minimal cross-section of the catheter at the location of the filter element 6 is obtained.

When the filter element 6 has been arranged in the required position inside the vena cava of the patient, the inner tube-like element 5 is moved in a proximal direction in relation to the outer tube-like element 3, so that the strips 7 come into contact with the wall of the vena cava 10. Thus, the strips bend outward to form a filter element which can remove and retain thrombi from the blood.

As illustrated, the tunica intima of the vena cava 10 is arranged around the strips 7 positioned against the wall of the vena cava, so that the strips are enclosed by the vena cava wall. When removing the catheter it will consequently not suffice to straighten the strips 7 again, as this would result in damage to the vena cava.

With the embodiment shown, the ends of the strips 7 which are connected to the supporting member 9 have been made detachable in order to prevent such damage. The ends 16 of the strips 7 have been fixed by detachable engaging means in the supporting member 9. To this end the supporting member 9 comprises a mounting or cavity 15 which has a radial width which is such that, for example, the strip end 16 may freely move in and out of the cavity 15. The radial outer wall of the cavity or mounting 15 has been provided with a bulge and the strip end 16 with a matching indentation. The blocking means 18, which is formed by a cylindrical tube section, extends inside the mounting 15 and leaves a space in the mounting 15 which has a shape which is complementary to that of the strip end 16. In the engaging position of the blocking means 18, illustrated in FIG. 2, in which the latter extends inside the mounting 15, the strip end 16 has been fixed to the supporting member 9, as the profile of the indentation and the bulge prevent unimpeded outward movement of the strip end 16.

When the catheter is to be removed, the strip ends 16 must be disengaged. This is done by moving the blocking means 18, which, as has been mentioned above, are connected to the inner tube-like element 4, to the right in relation to the supporting member 9 and consequently in relation to the inner tube-like element 5. As a result sufficient space is created inside the mounting 15 so that the strip end 16 will move out of the mounting 15. As can be seen in FIG. 4, the outer tube-like body 3 is subsequently moved in relation to the inner tube-like body 5 in the proximal direction, as a result of which, without any significant tensile force been applied, the strips 7 are released from the mounting 15 and the catheter with the filter element can be withdrawn. On pulling back, the strips slide through the tissue 11 which has grown around them without damaging the tissue.

Fitting the strip end 16 to the supporting member 9 is based on the fact that the strip end comprises a section 17 with a cross-section which decreases in the direction away from the end, that is to say towards the right as seen in the figure, and that the blocking means 18 in the engaging position leave space inside the mounting 15 the shape of which is complementary to the section 17.

The front supporting end 9 has been provided at its relatively proximal end with a pliable lip 19, which lies in a resilient manner against the strips when they are fixed. Thus a smooth transition is achieved between the supporting member 9 and the strips. The engaging means can be embodied in many different ways. The FIGS. 5 through 11 show a few possibilities.

Figure 5:
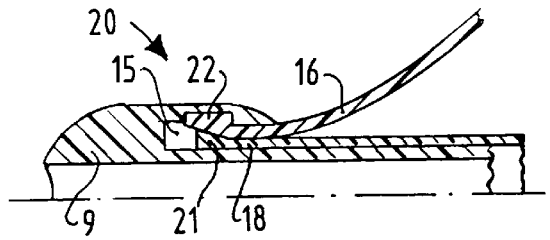

With the embodiment of the catheter 20 as shown in FIG. 5, the strip end has been provided with a projection 22 which engages in a groove inside the mounting 15 of the supporting member. In the engaging position moved to the right, the blocking means 18 comprise a wedge shaped end 21 which keeps the projection 22 pushed into the groove. In order to disconnect, the blocking means 18 are moved, as seen in the figure, towards the left, that is to say, are pushed further into the mounting 15, as a result of which the projection 22 can be released from the groove.

Figure 6:
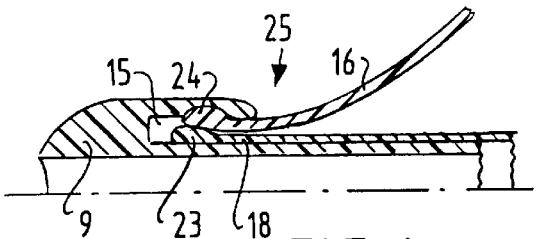

The embodiment of the catheter 25 as shown in FIG. 6 substantially corresponds to the one shown in FIG. 5. Also in this case the strip end 16 has been provided with a projection 24 which engages in an indentation of a wall of the mounting 15. The blocking means 18 have been provided at their relatively distal ends with a bulge 23 with which the strip end is kept pushed into the indentation. For the purpose of releasing the strip ends the blocking means 18 are moved to the left, as a result of which sufficient space is created to release the strip end.

Figure 7:
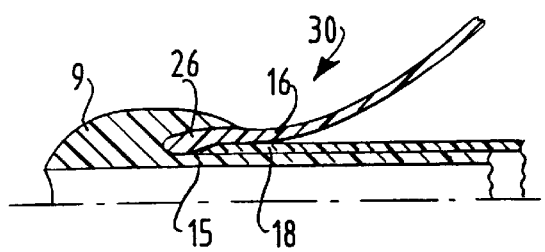

With the catheter 30 of FIG. 7 the strip end 16 has also been provided with a bulge 26 which is pushed into a mounting 15 of the supporting member. In this case the blocking means 18 form a simple sleeve which narrows the exit of the mounting 15, as a result of which the bulge 26 cannot move out of the mounting 15 as long as the blocking means 18 are in the engaging position illustrated. By simply moving the blocking means 18 to the right, sufficient space is created for the bulge 26 to pass and for the release of the strip end 16.

Figure 8:
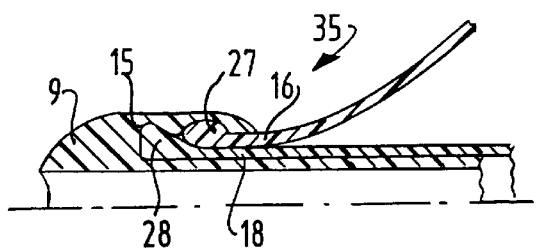

The catheter 35 as shown in FIG. 8 comprises engaging means which are based on a somewhat different principle. The strip end 16 has in this case been provided with a bulge 27 which slots into an indentation in the mounting of the supporting member. The blocking means 18 have however been provided with a rather pronounced wedge shaped end 28 which is associated with a complementary surface of the mounting 15. In the state illustrated in FIG. 8 both the strip end 16 and the blocking means 18 have been fixed. In order to release the strip end 16, the blocking means 18 are moved over a short distance to the right, as a result of which the wedge shaped end 28 pushes the section of the supporting member 9 adjoining the mounting 15 outwards, so that the bulge 27 can move out.

Figure 9:
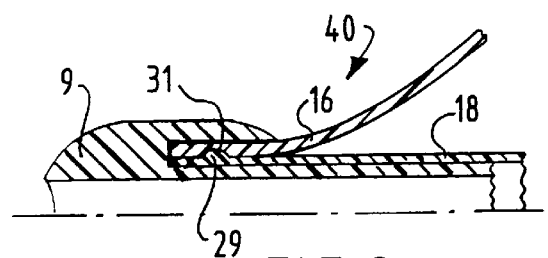

With the catheter 40 of FIG. 9, the blocking means 18 and the strip end 16 are provided with profiles which engage at right angles to the displacement direction extending from left to right of the blocking means 18. These profiles comprise a bulge 29 arranged on the blocking means 18 and a corresponding indentation arranged in the strip end 31. When the strip end 16 and the blocking means 18 have been inserted into the mounting as shown in FIG. 9, the strip end 16 is fixed in relation to the supporting member 9. Together with the blocking means 18, the strip end 16 can be moved freely inside the mounting so that, when the blocking means 18 are moved to the right from the engaging position shown into the disengaging position, the strip end 16 moves along and is consequently moved out of the mounting together with the blocking means 18.

Figure 10:
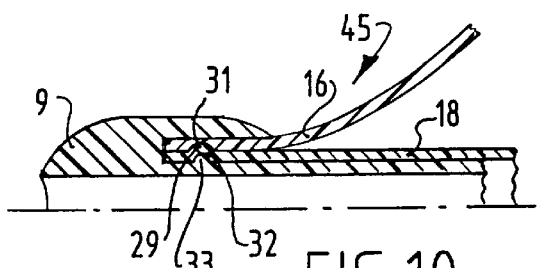

With the embodiment as shown in FIG. 10, the blocking means 18 have additionally been provided with an indentation 32 and the inner wall of the mounting with a corresponding bulge 33. As a result the blocking means 18 are retained together with the strip end 16 in the mounting of the supporting member 9 by means of snap action. When moving the blocking means 18 from the engaging position illustrated into the disengaging position, a certain resistance has to be overcome in order to pass the bulge 33. Subsequently the blocking means 18 move the strip end 16 outwards, free of the supporting member 9.

Figure 11:
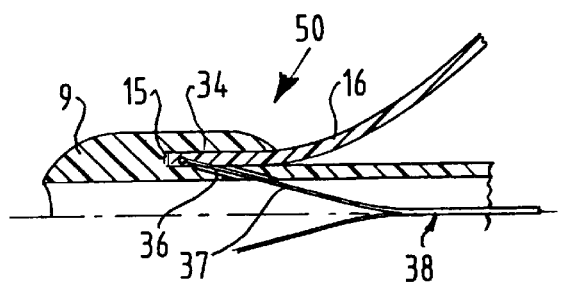

Finally, with the embodiment as shown in FIG. 11, comprising engaging means working according to yet another principle. The strip end 16 has also in this case been inserted into a mounting of the supporting member 9. In this case the engaging means comprise an oblique bore 34 in the strip end 16 and, in the inserted state of the strip end 16, a bore 36 in the supporting member 9, positioned in line with this bore 34. A stiff wire 37 has been introduced into these aligned bores 34 and 36. This wire 37 prevents the strip end 16 from moving outwards, out of the mounting 15.

For the purpose of disengaging the strip end 16, the catheter 50 has been provided with a pull wire 38 extending towards the proximal end, which has been connected to the blocking wire 37. By pulling at the pull wire 38 at the proximal end, the blocking wire 37 is moved from the engaging position illustrated into the disengaging position, in which it has been withdrawn from at least the oblique bore 34 in the strip end 16. The strip end 16 can then move freely outwards, out of the mounting 15.

It will be clear that the invention may take the form of various different embodiments. Although in the variations of embodiments the strip ends have been received in a mounting retainer, the invention is not limited to such embodiments. Any manner in which the strip ends are fixed to the mounting retainer and disconnected therefrom by separate engaging means could be used to carry out this operation.

Accordingly, the above description in conjunction with the attached drawings are for illustrative purposes only and are not intended to limit the scope of the invention, which is as defined in the claims below:

That which is claimed is:

1. An intravascular catheter filter system which comprises an outer cylindrical tubing having an inner lumen and distal and proximal ends; an intermediate cylindrical tubing slidably received by the outer cylindrical tubing and having an inner lumen and distal and proximal ends; and an inner cylindrical member slidably received by the intermediate cylindrical tubing and having distal and proximal ends; an expandable filter element comprising a plurality of arcuate, elongate, flexible strips having proximal ends attached to the distal end of the outer cylindrical tubing and being positioned adjacent to each other so as to be of a generally cylindrical configuration, said flexible strips being normally biased outwardly from the center of the cylindrical configuration; a cylindrical filter retaining member disposed on the distal end of the intermediate cylindrical tubing, said retaining member having a cylindrical slot for receiving the distal tips of the flexible strips of the filter element so that when said intermediate cylindrical tubing is moved proximally with respect to said outer cylindrical tubing the flexible strip are bowed outwardly to form a generally bulbus configuration of flexible strips; and, a locking member disposed on the distal end of the inner cylindrical member for normally locking the distal tips of the flexible strips into the cylindrical slot of the retaining member, and upon movement of the inner cylindrical member relative to the intermediate cylindrical tubing, unlocking the distal tips of the flexible strips from the cylindrical slot in the retaining member in order to free the distal tips of the flexible strips to thereby assist in the removal of the catheter filter from a vessel.

2. An intravascular catheter filter system as defined in claim 1, wherein said locking member has a distal tip which is also received by the cylindrical slot in the retaining members to thereby releasably lock the distal tip of the flexible strips into the cylindrical slot of the retaining member.

3. A intravascular catheter filter system as defined in claim 2, wherein the tips of the flexible strips each have an indention in the wall surface of the flexible strip, and the wall surface of the cylindrical slot in the retaining member is provided with corresponding projections which engage the indentions in the wall surface of the flexible strips, and the locking member slidably engages the opposite wall surface of the distal ends of the flexible strips and the opposite wall surface of the cylindrical slot to thereby maintain the engagement between the corresponding projections in the cylindrical slot and the indentions in the distal end of corresponding flexible strips.

4. A intravascular catheter filter system as defined in claim 2, wherein the tips of the flexible strips each have a projection which extends from the wall surface of the flexible strip, and the wall surface of the cylindrical slot in the retaining member is provided with corresponding indentions which engage the projections from the wall surface of the flexible strips, and the locking member slidably engages the opposite wall surface of the distal ends of the flexible strips and the opposite wall surface of the cylindrical slot to thereby maintain the engagement between the corresponding projections from the surface of the flexible strips and the indentions in the wall surface of the cylindrical slot.

5. An intravascular catheter filter system as defined in claim 1, wherein the tips of the flexible strips each have restraining means for engaging the wall surface of the cylindrical slot, and the locking member contacts the surface of the flexible strips to cause the restraining means to engage the wall surface of the cylindrical slot.

\* \* \* \* \*